(12) United States Patent
Dean et al.

(10) Patent No.: US 7,138,493 B1
(45) Date of Patent: Nov. 21, 2006

(54) ATP-BINDING CASSETTE PROTEIN RESPONSIBLE FOR CYTOTOXIN RESISTANCE

(75) Inventors: Michael Dean, Frederick, MD (US); Rando L. Allikmets, Cornwall-on-the-Hudson, NY (US); Susan E. Bates, Bethesda, MD (US); Antonio T. Fojo, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/856,927

(22) PCT Filed: Nov. 24, 1999

(86) PCT No.: PCT/US99/28107

§ 371 (c)(1),
(2), (4) Date: Sep. 19, 2001

(87) PCT Pub. No.: WO00/36101

PCT Pub. Date: Jun. 22, 2000

Related U.S. Application Data

(60) Provisional application No. 60/110,473, filed on Nov. 30, 1998.

(51) Int. Cl.
*C07K 5/00* (2006.01)
(52) U.S. Cl. .................. 530/350; 530/389.1; 536/23.1; 536/23.5
(58) Field of Classification Search ................ 530/350, 530/389.1; 536/23.1, 23.5
See application file for complete search history.

(56) References Cited

U.S. PATENT DOCUMENTS 6,313,277 B1 * 11/2001 Ross et al.

FOREIGN PATENT DOCUMENTS

| WO | WO 98/55614 A2 | 12/1998 |
| WO | 04110 * | 8/1999 |
| WO | WO 99/40110 A1 | 8/1999 |

OTHER PUBLICATIONS

Allikmets et al., "Characterization of the human ABC superfamily: isolation and mapping of 21 new genes using the Expressed Sequence Tags database", *Human Molecular Genetics* 5:10: 1649-1655 (1996).
Lee et al., "Reduced Drug Accumulation and Multidrug Resistance in Human Breast Cancer Cells Without Assocaited P-Glycoprotein or MRP Overexpression", *Journal of Cellular Biochemistry* 65: 513-526 (1997).
Doyle et al., "Cloning and characterization of Breast Cancer Resistatance Protein (BCRP), a novel ATP-binding cassette (ABC) transporter that may contribute to the multidrug-resistance phenotype of MCF-7/AdrVp breast cancer cells", *Proceedings of the American Association for Cancer Research* 39: 657 (1998).
Lage et al., "Cloning and characterization of human cDNAs encoding a protein with high homology to rat intestinal development protein OCI-5", *Gene* 188: 151-156 (1997).
Bruin et al., "Reversal of resistance by GF120918 in cell lines expressing the ABC half-transporter, MXR", *Cancer letters* 146: 117-126 (1999).
Miyake et al., "Molecular Cloning of cDNAs Which are Highly Overexpressed in Mitoxantrone-resistant cells: Demonstration of Homology to ABC Transport Genes", *Cancer Research* 59: 8-13 (1999).
Allikmets et al., "A Human Placenta-specific ATP-Binding Cassette Gene (ABCP) on Chromosome 4q22 That is Involved in Multidrug Resistance", *Cancer Research* 58: 5337-5339 (1998).
Doyle et al., "A multidrug resistance transporter from human MCF-7 breast cancer cells", *Proc. Natl. Acad. Sci. USA* 95: 15665-15670 (1998).

* cited by examiner

*Primary Examiner*—Sheela J. Huff
(74) *Attorney, Agent, or Firm*—Townsend and Townsend and Crew LLP

(57) ABSTRACT

This invention provides for a novel ATP-binding cassette protein which is responsible for cytotoxin resistance. The invention also provides for methods of expressing the protein and assays for identification of inhibitors of the protein.

4 Claims, No Drawings

US 7,138,493 B1

ATP-BINDING CASSETTE PROTEIN RESPONSIBLE FOR CYTOTOXIN RESISTANCE

This application is a 371 of PCT/US99/28107 filed Nov. 24, 1999, which claims priority to provisional application No. 60/110,473, filed Nov. 30, 1998.

FIELD OF THE INVENTION

This invention provides for a novel ATP-binding cassette protein which is responsible for cytotoxin resistance. The invention also provides for methods of expressing the protein and assays for identification of inhibitors of the protein.

RELATED APPLICATIONS

There are no related applications.

BACKGROUND OF THE INVENTION

The multidrug resistance/ATP-binding cassette (MDR/ABC) superfamily in humans includes genes whose products represent membrane proteins involved in energy-dependent transport of a wide variety of substrates across a membrane (see, e.g., Dean, M. and Allikmets, R. (1995) Curr. Opin. Genet. Dev. 5, 79–785). The overexpression of ABC transporters has been linked with drug resistance since the 1976 discovery of P-glycoprotein and the subsequent cloning of the encoding gene, MDR-1. Resistance ensues from reduced intracellular drug concentrations, a result of active drug efflux. The subsequent identification of the multidrug resistance associated protein (MRP), encoded by the MRP gene, heralded a new era that recognized the complexity of the problem and catalyzed the search for additional transporters. MDR-1 and MRP are members of the expanding superfamily of ATP-binding cassette proteins (ABC proteins). This superfamily is comprised of a large and diverse group of proteins that transport solutes across biological membranes. Transmembrane domains are thought to form a pathway through which substrates cross cell membranes, while two ATP-binding domains hydrolyze ATP to accomplish substrate transport. Mutations in ABC transporters have been identified as etiologic in diseases including hyperinsulinemic hypoglycemia of infancy, adrenoleukodystrophy, and cystic fibrosis. The transporters MDR-1 and MRP, and possibly the multispecific organic anion transporter, cMOAT, are thought to be involved in both normal excretion of xenobiotics and in drug resistance. The ABC superfamily also includes a number of transporters without known function and the potential exists to identify additional transporters which mediate drug resistance.

Recent studies have described a number of cell lines with resistance to mitoxantrone that exhibit multidrug resistance without overexpression of MRP. In addition to mitoxantrone, these cell lines are particularly resistant to anthracyclines, and a have an energy-dependent reduction in the accumulation of daunomycin and mitoxantrone. Cell lines possessing this phenotype include sublines derived by selection of leukemic cells, as well as breast, colon, and gastric carcinomas.

SUMMARY OF THE INVENTION

The present invention thus provides for the first time, nucleic acids encoding a new transporter protein that mediates drug resistance. These proteins are generically called ATP binding cassette proteins (ABC proteins). The ABC protein of the invention is referred to as MXR1. It is also known as ABCP, and is also known as ABCG2.

In one aspect, the present invention provides an isolated ATP-binding cassette protein that confers mitoxantrone resistance to S1-M1-80 human colon carcin-oma cells when expressed in the cells; and specifically binds to polyclonal antibodies which specifically bind to a member of the group of proteins depicted in SEQ ID NO. 2 or SEQ ID. NO. 4; and has a molecular weight between about 70 kDa and about 75 kDa.

In one embodiment, the MXR1 protein has the sequence depicted in SEQ ID NO. 2 or SEQ ID NO. 4. In another embodiment, the protein has 95% identity to the amino acids depicted in SEQ ID NO. 2 or SEQ ID. NO. 4.

In another aspect, the present invention provides a eukaryotic cell genetically altered to overexpress an ATP-binding cassette protein that confers mitoxantrone resistance on S1-M1-80 human colon carcinoma cells when expressed in the cells; and specifically binds to polyclonal antibodies which specifically bind to a member of the group of proteins depicted in SEQ ID NO. 2 or SEQ ID. NO. 4.

In one embodiment, the cells of the invention are genetically altered by transformation of the cell with an exogenous DNA comprising an expression cassette encoding the ATP-binding cassette protein. In another embodiment, the expression cassette also employs a heterologous promoter operatively linked to the DNA encoding the ATP-binding cassette protein. In another embodiment, the cell may have an endogenous copy of the ATP-binding cassette protein with a genetic alteration comprising insertion of DNA that serves as an enhancing element or as a second promoter where the insertion is upstream of the endogenous promoter operatively linked to the ATP-binding cassette protein and where the inserted DNA increases the basal expression levels of ATP-binding cassette protein.

In another aspect, the present invention provides for DNA encoding an ATP-binding cassette protein wherein the protein confers mitoxantrone resistance on S1-M1-80 human colon carcinoma cells when expressed in the cells and specifically binds to polyclonal antibodies which specifically bind to the proteins depicted in SEQ ID NO. 2 or SEQ ID NO. 4.

In one embodiment, the DNA encodes for the protein of SEQ ID NO. 2 or SEQ ID NO. 4 and in other embodiments the DNA encodes a protein that has 95% identity to the amino acids depicted in SEQ ID NO. 2 or SEQ ID NO. 4. In another embodiment, the DNA has the sequence depicted in SEQ ID NO. 1 or SEQ ID NO. 3.

In another aspect, the present invention provides a process for over expressing ATP-binding cassette protein in a cell comprising a first step of either (1) transforming the cell with an expression cassette which directs the expression of ATP-binding cassette protein; or, (2) selecting a cell having an endogenous copy of the ATP-binding cassette protein, and transforming the cell with DNA which can serve as an enhancing element or as a second promoter where the insertion is upstream of the endogenous promoter operatively linked to the ATP-binding cassette protein and where the inserted DNA increases the basal expression levels of ATP-binding cassette protein; and a second step of culturing the transformed cell under conditions where the levels of ATP-binding cassette protein are increased above the basal levels of the non-transformed cells. The ATP binding protein of this embodiment is one that confers mitoxantrone resistance on S1-M1-80 human colon carcinoma cells when expressed in the cells; and, specifically binds to polyclonal antibodies which specifically bind to a member of the group of proteins depicted in SEQ ID NO. 2 or SEQ ID No. 4.

In one embodiment, the ATP binding cassette protein has 95% homology to the amino acids depicted in SEQ ID NO. 2 or SEQ ID No. 4. In yet another embodiment, the protein has the amino acids depicted in SEQ ID NO. 2 or SEQ ID No. 4.

In another aspect, the present invention provides a method of screening for inhibitors of cytotoxin resistance in cells. The method comprises (1) culturing a cell genetically altered by the introduction of heterologous DNA which permits the overexpression an ATP-binding cassette protein that confers mitoxantrone resistance on S1-M1-80 human colon carcinoma cells when expressed in the cells; and specifically binds to polyclonal antibodies which specifically bind to a member of the group of proteins depicted in SEQ ID NO. 2 or SEQ ID NO. 4; and, (2) contacting the cell with a cytotoxin in an amount that permits cell survival due to the resistance conferred by the ATP-binding cassette protein; and, (3) contacting the cell with a compound that inhibits the biological activity of the ATP-binding cassette protein; and, (4) detecting the inhibition by measuring growth inhibition of the cells.

In one embodiment, the cytotoxin is mitoxantrone. In another embodiment, the cytotoxin is daunomycin. In another embodiment, the cell is a carcinoma cell. In another embodiment, the ATP-binding cassette protein has 95% homology to the amino acids depicted in SEQ ID NO. 2 or SEQ ID NO. 4. In another embodiment, the ATP binding cassette protein has the amino acid sequence depicted in SEQ ID NO. 2 or SEQ ID NO. 4.

In another aspect, the invention provides a binding protein that specifically binds to an ATP-binding cassette protein which has 95% homology to the amino acids depicted in SEQ ID NO. 2 or SEQ ID NO. 4. In one embodiment, the binding protein is an antibody, and in another embodiment, the binding protein is a monoclonal antibody.

Non-Competitive Assay Formats

Immunoassays for detecting the ATP binding cassette protein may be either competitive or noncompetitive. Noncompetitive immunoassays are assays in which the amount of captured analyte (in this case the protein) is directly measured. In one preferred "sandwich" assay, for example, the capture agent (anti-ABC antibodies) can be bound directly to a solid substrate where they are immobilized. These immobilized antibodies then capture the ATP binding cassette protein present in the test sample. The ATP binding cassette protein thus immobilized is then bound by a labeling agent, such as a second ATP binding cassette antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

DETAILED DESCRIPTION

Introduction

The present invention provides for the first time, nucleic acids encoding the ATP binding cassette (ABC) protein, MXR1. These nucleic acids and the subunits they encode are part of a superfamily of membrane proteins and a part of a multidrug resistance subfamily, involved in energy dependent transport of substrates across membranes. The gene which is the subject of the present invention encodes a 658 amino acid protein that is highly expressed in placenta, in fetal brain and liver, and in at least two mitoxantrone resistant cancer cell lines. The strong expression of the gene in the placenta indicates that the MXR1 protein is important in the transfer of specific molecules in or out of the placenta. The overexpression in the cancer cell lines indicates that the protein is involved with multidrug resistance in cancer cells.

The invention also provides an assay for screening for inhibitors of cytotoxin resistance in cells. The assay involves culturing a cell that has been genetically altered by the introduction of heterologous DNA which permits the overexpression of an ATP-binding cassette protein that confers mitoxantrone resistance and contacting the cell with a cytotoxin and contacting the cell with a compound that inhibits the biological activity of the ATP-binding cassette protein and detecting the inhibition by measuring growth inhibition of the cells.

Definitions

"ATP-binding cassette protein" refers to a protein having an ATP-binding cassette (ABC) (see, e.g., Allikmets et al., Human Molecular Genetics 5;1649–1655 (1996)) which is involved in transporting substrates across cell membranes. They are energy dependent (ATP) and have defined transmembrane domains.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the F(ab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879–5883. While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage (e.g., scFv, Fv, Fab and disulfide linked Fv (Reiter et al. (1995) Protein Eng. 8: 1323–1331). Antibodies can also include diantibodies and miniantibodies.

An "anti-M11" or an "anti-ABC" antibody is an antibody or antibody fragment that specifically binds an M1 preotein or an ATP-binding cassette protein respectively.

"Binding protein" is a general term for a protein that specifically binds to a target ligand or cognate molecule. It includes either member of a binding pair. It would also include receptor-like molecules, hormones, antibodies, antigens, and importantly proteins identified as selective or specific binders from a randomized library of proteins displayed on phage.

"Endogenous" refers to a naturally occurring element of a cell or organism that is naturally produced by the cell or organism as part of its normal life cycle.

"Exogenous" refers to non-naturally occurring elements of a cell which are introduced by the hand of man. Transformation of cell with nucleic acid introduces exogenous DNA elements. An exogenous DNA element usually denotes a nucleic acid that has been isolated, cloned, and ligated to a nucleic acid with which it is not combined in nature, and or introduced into and/or expressed in a cell or cellular environment other than the cell or cellular environment in which said nucleic acid or protein may be found in nature. The term encompasses both nucleic acids originally obtained from a different organism or cell type than the cell type in which it is expressed, and also nucleic acids that are obtained from the same cell line as the cell line in which it is expressed.

A prokaryotic cell has been "transformed" by an exogenous nucleic acid when such exogenous nucleic acid has been introduced inside the cell membrane. Exogenous DNA may or may not be integrated (covalently linked) into chromosomal DNA making up the genome of the cell. The exogenous DNA may be maintained on an episomal element, such as a plasmid.

An "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "over expression" refers to the situation when one or more components of cell may be present at a higher than normal cellular level (i.e., higher than the concentration known to usually be present in the cell type exhibiting the protein complex of interest). For example, the gene encoding a protein may begin to be overexpressed, or may be amplified (i.e., its gene copy number may be increased) in certain cells, leading to an increased number of component molecules within these cells. Typically overexpression will result in from about 10% to about 15% over the basal expression level.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant)

form of the cell or express native genes that are otherwise abnormally expressed, under expressed or not expressed at all.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence, which has a designated percent sequence or subsequence complementarity when the test sequence has a designated or substantial identity to a reference sequence. For example, a designated amino acid percent identity of 86% refers to sequences or subsequences that have at least about 86% amino acid identity when aligned for maximum correspondence over a comparison window as measured using one of the following sequence comparison algorithms or by manual alignment and visual inspection. Preferably, the percent identity exists over a region of the sequence that is at least about 25 amino acids in length, more preferably over a region that is 50 amino acids in length.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters.

A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithm that is suitable for determining percent sequence identity (i.e., substantial similarity or identity) is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to an ATP binding cassette nucleic acid sequence, such as MXR1, if the smallest sum probability in a comparison of the test nucleic acid to the MXR1 nucleic acid is less than about 0.1, more preferably less than about 0.01, and most preferably less than about 0.001.

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues.

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity. For determination of specific binding of an anti-ABC antibody, an immunoblot assay is preferred.

A "conservative substitution," when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W.H. Freeman and Company. One of skill in the art will appreciate that the above-identified substitutions are not the only possible conservative substitutions. For example, one may regard all charged amino acids as conservative substitutions for each other whether they are positive or negative. In addition, individual substitutions, deletions or additions which alter, add or delete a single amino acid or a small percentage of amino acids in an encoded sequence are also "conservatively modified variations".

The terms "isolated," "purified," or "biologically pure" refer to material that is substantially or essentially free from components that normally accompany it as found in the native state.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment.

Typically, the expression vector includes a nucleic acid to be transcribed or operably linked to a promoter.

The phrase "a nucleic acid sequence encoding" refers to a nucleic acid which contains sequence information for a structural RNA such as rRNA, a tRNA, or the primary amino acid sequence of a specific protein or peptide, or a binding site for a transacting regulatory agent. This phrase specifically encompasses degenerate codons (i.e., different codons which encode a single amino acid) of the native sequence or sequences which may be introduced to conform with codon preference in a specific host cell.

"Antisense sequence or antisense nucleic acids" are used interchangeably and refer to sequences of nucleic acids that are complementary to the coding mRNA nucleic acid sequence. The phrase specifically encompasses nucleic acid sequences that bind to mRNA or portions thereof to block transcription of mRNA by ribosomes.

"Conferring mitoxantrone resistance" refers to the situation in which the expression of a protein in a cell makes the cell resistant to a particular drug or antibiotic. For example, cells where an ABC gene is overexpressed or amplified in certain breast and colon cancer cell lines will be resistant to the chemotherapeutic drug mitoxantrone, and to a lesser extent daunorubicin, i.e., the drugs will have no effect on the cell.

"Genetically altered" refers to a protein, cell, nucleic acid or other biological molecule that has been recombinantly or otherwise manipulated such that it is no longer in its native state.

The phrase "basal expression levels" refers to the normal, base or fundamental level of protein expression in a cell in its usual environment.

"Enhancing element" refers to a component in a cell that enhances or increases the basal or normal protein expression level. Such an element will cause a cell to express more of a protein than it would under natural or normal conditions.

"Growth inhibition" refers to cell death or a slowing down or suppression of cell growth, biological function, or division. The growth inhibition can be caused by chemical or physical means.

Genes Encoding ATP-Binding Cassette Protein

A. General Recombinant DNA Methods

This invention relies on routine techniques in the field of recombinant genetics to produce the MXR1 nucleic acids of the present invention. Basic texts disclosing the general methods of use in this invention include Sambrook et al., *Molecular Cloning, A Laboratory Manual* (2$^{nd}$ ed. 1989); Kriegler, *Gene Transfer and Expression: A Laboratory Manual* (1990); and *Current Protocols in Molecular Biology* (Ausubel et al., eds., 1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized according to the solid phase phosporamidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion exchange HPLC as described in Pearson & Reanier, J. Chrom. 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding MXR1

In general, the nucleic acid sequences encoding the ATP binding cassette proteins and related nucleic acid homologs are cloned from cDNA and genomic DNA libraries by hybridization with a probe, or isolated using amplification techniques with oligonucleotide primers. For example, ABC proteins are typically isolated from mammalian DNA libraries by hybridizing with a nucleic acid probe, the sequence of which can be derived from SEQ ID NO: 1 or 3. A suitable tissue from which ABC proteins and cDNA can be isolated is fetal brain or liver, and preferably placenta.

Amplification techniques using primers can also be used to amplify and isolate ABC nucleic acids from DNA or RNA. The degenerate primers encoding the following amino acid sequences can also be use to amplify a sequence of MXR1. SEQ ID NOS: 5 & 6 (Dieffanfach & Dveksler, *PCR Primer: A Laboratory Manual* (1995)). These primers can be used, e.g., to amplify either the full length sequence or a probe of one to a hundred nucleotides, which is then used to screen a mammalian library for full length MXR1.

Nucleic acids encoding ABC proteins can also be isolated from expression libraries using antibodies as probes. Such polyclonal or monoclonal antibodies can be raised using the sequence of SEQ ID NO: 2 or 4

MXR1 polymorphic variants, alleles, and interspecies homologs that are substantially identical to MXR1 can also be isolated using MXR1 nucleic acid probes, and oligonucleotides under stringent hybridization conditions, by screening libraries. Alternatively, expression libraries can be used to clone MXR1 polymorphic variants, alleles, and interspecies homologs, by detecting homologs immunologically with antisera or purified antibodies made against MXR1, which also recognize and selectively bind to the MXR1 homolog.

To make a cDNA library, one should choose a source that is rich in the MXR1 mRNA, e.g., human colon carcinoma cells. Placenta tissue or fetal brain or liver tissue. The mRNA is then made into cDNA using reverse transcriptase, ligated into a recombinant vector, and transfected into a recombinant host for propagation, screening, and cloning. Methods for making and screening cDNA libraries are well known (see, e.g., Gubler & Hoffman, *Gene* 25:263–269 (1983); Sambrook et al. supra; Ausubel et al., supra).

An alternative method of isolating MXR1 nucleic acids and their homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds 1990)). Methods such as polymerase chain reaction (PCR) and ligase chain reaction (LCR) can be used to amplify nucleic acid sequences of ABC proteins directly from mRNA, from cDNA, from genomic libraries or cDNA libraries. Degenerate oligonucleotides can be designed to amplify ABC homologs using the sequences provided herein. Restriction endonuclease sites can be incorporated into the primers. PCR or other in vitro amplification methods may be useful, for example, to clone nucleic acid sequences that code for proteins to be expressed, to make nucleic acids to use as probes for detecting the presence of ABC protein encoding mRNA in physiological samples, for nucleic acid sequencing, or for other purposes. Genes amplified by the PCR reaction can be purified from agarose gels and cloned into an appropriate vector.

Gene expression of ABC proteins can also be analyzed by techniques known in the art, e.g., reverse transcription and amplification of mRNA, isolation of total RNA or polyA$^+$ RNA, northern blotting, dot blotting, in situ hybridization, RNAse protection, probing DNA microchip arrays, and the like.

Synthetic oligonucleotides can be used to construct recombinant ABC genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the ABC nucleic acid. The specific subsequence is then ligated into an expression vector.

The nucleic acid encoding the MXR1 protein is typically cloned into intermediate vectors before transformation into prokaryotic or eukaryotic cells for replication and/or expression. These intermediate vectors are typically prokaryote vectors, e.g., plasmids or shuttle vectors.

Expression of ATP-Binding Cassette Proteins

To obtain high level expression of a cloned gene or nucleic acid, such as those cDNAs encoding the ABC protein MXR1, one typically subclones MXR1 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing MXR1 are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the MXR1 encoding nucleic acid in host cells. A typical expression cassette thus contains a promoter operably linked to the nucleic acid sequence encoding an ABC protein and signals required for efficient polyadenylation of the transcript, ribosome binding sites, and translation termination. The nucleic acid sequence encoding MXR1 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with an MXR1 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of MXR1 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing MXR1 protein.

Another mode of expression for ABC proteins involves transactivation, which describes a method of activating (i.e., turning on) and amplifying an endogenous gene encoding a desired product, such as MXR1, in a transfected cell (See, e.g., U.S. Pat. No. 5,733,761).

DNA sequences that are not normally functionally linked to the endogenous gene, can be introduced by homologous recombination with genomic DNA. The DNA sequences would be inserted into the host genome at or near the endogenous gene and serve to alter (e.g., activate) the expression of the endogenous gene and further allow selection of cells in which the activated endogenous gene is amplified.

The transactivation can be used to target different events in the cell by a simple insertion of a regulatory sequence that places the endogenous gene under the control of the new regulatory sequence (for example, by insertion of either a promoter or an enhancer, both upstream of an endogenous gene). Additionally the transactivation protocols can be used to delete a regulatory element or replace an existing element. For example, a tissue specific enhancer can be replaced by an enhancer that has broader or different cell-type specificity. In all cases, the targeting event can be identified by the use of one or more selectable markers that are physically associated with the targeting DNA sequence, allowing for selection of cells in which the exogenous DNA sequence has been integrated into the host cell genome. (see, e.g., U.S. Pat. No. 5,733,761.)

In another embodiment, the invention includes polymorphic alleles of MXR1. In addition, those of skill can readily create muteins or analogs of MXR1 based on comparisons with the mouse sequence of SEQ ID NO: 4 and conservative amino acid substitutions. When compared to SEQ ID NO: 2, a protein that exhibits conservative substitutions, as described above, is a protein of the invention. Such substitutions will alter the sequence of the protein from that provided in SEQ ID NO:2, but will not markedly change the biological activity of the molecule. For example, the serine at position 519 may be changed to a threonine; the alanine at position 529 may be changed to a threonine; the isoleucine at position 550 may be changed to leucine; and the alanine at position 597 may be changed to valine. These substitutions are provided by way of illustration and for clarity of understanding and not by way of limitation. It will be readily apparent to those of ordinary skill in the art, in light of the teachings of the invention, that certain changes may be made to the MXR1 protein sequence without changing its biological activity.

After the expression vector is introduced into the cells, the transfected cells are cultured under conditions favoring expression of MXR1 proteins, which are recovered from the culture using standard techniques identified below.

Purification of ATP-Binding Cassette Proteins

Once expressed the MXR1 proteins can be purified. Either naturally occurring or recombinant MXR1 protein can be purified for use in functional assays. Preferably, recombinant MXR1 is purified. Naturally occurring MXR1 protein is purified, e.g., from mammalian tissue such as placenta, fetal brain or liver tissues and any other source of an MXR1 homolog. Recombinant MXR1 is purified from any suitable expression system.

MXR1 may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant MXR1 is being purified. For example, proteins having established molecular adhesion properties can be reversibly fused to MXR1. With the appropriate ligand, MXR1 can be selectively adsorbed to a purification column and then freed from the column in a relatively pure form. The fused protein is then removed by enzymatic activity. Finally, MXR1 protein could be purified using immunoaffinity columns.

A. Purification of MXR1 from Recombinant Bacteria

Recombinant proteins are expressed by transformed bacteria in large amounts, typically after promoter induction, but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of MXR1 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. MXR1 is separated from other bacterial proteins by standard separation techniques, e.g., with Ni-NTA agarose resin.

Alternatively, it is possible to purify MXR1 protein from bacteria periplasm. After lysis of the bacteria, when MXR1 is exported into the periplasm of the bacteria, the periplasmic fraction of the bacteria can be isolated by cold osmotic shock in addition to other methods known to those of skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying MXR1 Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of MXR1 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

MXR1 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Antisense Applications For ATP-Binding Cassette Proteins

Gene regulation in MXR1 can be downregulated or entirely inhibited by the use of antisense molecules. An "antisense sequence or antisense nucleic acid" is a nucleic acid that is complementary to the coding MXR1 mRNA nucleic acid sequence or a subsequence thereof. Binding of the antisense molecule to the MXR1 mRNA interferes with normal translation of MXR1. The antisense molecule can be an endogenous or an exogenous complement to an mRNA. It can also be ribozyme or a ribozyme combined with a mRNA complement.

In conventional antisense technology, a nucleic acid segment from the desired gene is cloned and operably linked to a promoter sequence such that the anti-sense strand of RNA will be transcribed. The construct is then transformed into cells and the anti-sense strand of RNA is produced. (see, e.g., Sheehy et al., Proc. Nat. Acad. Sci. USA 85:8805–8809 (1988), and Hiatt, et al., U.S. Pat. No. 4,801,340.)

The nucleic acid segment to be introduced in antisense suppression generally will be substantially identical to at least a portion of the endogenous gene or gene to be repressed, but need not be identical. The vectors can thus be designed such that the inhibitory effect applies to other proteins within a family of genes exhibiting homology or substantial homology to the target gene. The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

Absolute complementarity of the antisense molecule, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense oligonucleotides complementary to mRNA coding regions are less efficient inhibitors of translation than oligonucleotides that are complementary to 5'- or 3'-untranslated sequence, but should be used in accordance with the instant invention. The antisense nucleic acids should be at least six nucleotides in length, and are preferably oligonucleotides ranging from 6 to about 50 nucleotides in length. In specific aspects, the oligonucleotide is at least 10 nucleotides, preferably at least 17 nucleotides, more preferably at least 25 nucleotides or most preferably at least 50 nucleotides.

Thus, in accordance with preferred embodiments of this invention, preferred antisense molecules include oligonucleotides and oligonucleotide analogs that are hybridizable with MXR1 mRNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of MXR1 polypeptides.

The mechanisms above also work with exogenous antisense molecules that are modified to be nuclease resistant. Therefore, in the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species which are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Oligonucleotides may also include species which include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of MXR1 to inhibit the function of that RNA.

The oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. It is also will known to prepare other oligonucleotide such as phosphorothioates and alkylated derivatives.

Catalytic RNA molecules or ribozymes can be used as a means to inhibit expression of endogenous genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Ribozymes include but are not limited to any of the various types, such as hairpin or hammerhead ribozymes. The design and use of target RNA-specific ribozymes is described in Haseloff et al., Nature, 334:585–591 (1988).

Antibodies Binding ATP-Binding Cassette Proteins

Methods of producing polyclonal and monoclonal antibodies that react specifically with MXR1 are known to those of skill in the art. See, e.g., Coligan (1991), CURRENT PROTOCOLS IN IMMUNOLOGY, Wiley/Greene, NY; and Harlow and Lane; Stites et al. (eds.) *BASIC AND CLINICAL IMMUNOLOGY* (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature,* 256:495–497. Such techniques include antibody preparation by selection of antibodies from libraries of recombinant antibodies in phage or similar vectors. See, Huse et al. (1989), *Science,* 246: 1275–1281; and Ward et al. (1989), *Nature,* 341:544–546. For example, in order to produce antisera for use in an immunoassay, the ATP binding cassette polypeptide partially encoded by SEQ ID NO: 1 or 3 or a fragment thereof, is isolated as described herein. For example, recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-ATP binding cassette protein, MXR1, or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of MXR1 comprising immunogens may be used to produce antibodies specifically reactive with MXR1. Recombinant protein is the preferred immunogen for the production of monoclonal or polyclonal antibodies. Naturally occurring protein may also be used either in pure or impure form. Synthetic peptides made using the protein sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the ATP binding cassette protein, MXR1. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology,* 14: 309–314).

Single chain recombinant versions of antibodies, against predetermined fragments of ABC polypeptides, such as MXR1, are raised by immunizing animals, e.g., with conjugates of the fragments with carrier proteins as described above. Typically, the immunogen of interest is a peptide of at least about 5 amino acids, more typically the peptide is 10 amino acids in length, preferably, the fragment is 15 amino acids in length and more preferably the fragment is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Once specific antibodies are available, a particular protein, such as MXR1, can be detected by a variety of immunoassay methods. For a review of immunological and immunoassay procedures in general, see *Basic and Clinical Immunology* 7th Edition (D. Stites and A. Terr ed.) 1991. Moreover, the immunoassays of the present invention can be performed in any of several configurations, which are reviewed extensively in *Enzyme Immunoassay,* E. T. Maggio, ed., CRC Press, Boca Raton, Fla. (1980); "Practice and Theory of Enzyme Immunoassays," Tijssen; and, Harlow and Lane, each of which is incorporated herein by reference.

Immunoassays to ATP binding cassette protein MXR1 of the present invention may use a polyclonal antiserum which was raised to the protein partially encoded by SEQ ID NO: 1, or a fragment thereof. This antiserum is selected to have low crossreactivity against other non-ATP binding casette proteins and any such crossreactivity is removed by immunoabsorption prior to use in the immunoassay.

In order to produce antisera for use in an immunoassay, the ATP binding cassette protein of this invention or a fragment thereof, is isolated as described herein. For example, recombinant protein is produced in a transformed cell line. An inbred strain of mice such as Balb/c is immunized with the protein or a peptide using a standard adjuvant, such as Freund's adjuvant, and a standard mouse immunization protocol. Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-MXR1 ABC proteins, such as the human white gene homolog (see, e.g., Croop, J. M. et al. Gene (1997) 185 (1):77–85) using a competitive binding immunoassay such as the one described in Harlow and Lane, supra, at pages 570–573 and below.

Immunological Binding Assays

In a preferred embodiment, the ATP binding cassette protein is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology,* Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case the ATP binding cassette protein or subsequence). The capture agent is a moiety that specifically binds to the analyte. In a preferred embodiment, the capture agent is an antibody that specifically binds the ATP binding cassette protein. The antibody (anti- ABC protein MXR1) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled ATP binding cassette polypeptide or a labeled anti-ATP binding cassette antibody. Alternatively, the labeling agent may be a third moiety, such as another antibody, that specifically binds to the antibody/ATP binding cassette complex.

In a preferred embodiment, the labeling agent is a second human ATP binding cassette antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom, et al. (1985) *J. Immunol.,* 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Competitive Assay Formats

In competitive assays, the amount of analyte (ATP binding cassette protein) present in the sample is measured indirectly by measuring the amount of an added (exogenous) analyte (i.e., the ATP binding cassette protein) displaced (or competed away) from a capture agent (anti ABC antibody) by the analyte present in the sample. In one competitive assay, a known amount of, in this case, the ATP binding cassette protein, MXR1 is added to the sample and the sample is then contacted with a capture agent, in this case an antibody that specifically binds to MXR1. The amount of MXR1 bound to the antibody is inversely proportional to the concentration of M1 present in the sample.

In a particularly preferred embodiment, the antibody is immobilized on a solid substrate. The amount of the MXR1 bound to the antibody may be determined either by measuring the amount of MXR1 present in an MXR1/antibody complex, or alternatively by measuring the amount of remaining uncomplexed protein. The amount of MXR1 protein may be detected by providing a labeled MXR1 molecule.

A hapten inhibition assay is another preferred competitive assay. In this assay a known analyte, in this case the ATP binding casette protein, MXR1 is immobilized on a solid substrate. A known amount of anti-M1 antibody is added to the sample, and the sample is then contacted with the immobilized MXR1. In this case, the amount of anti-MXR1 antibody bound to the immobilized MXR1 is inversely proportional to the amount of MXR1 present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, the protein of SEQ ID NO:2 can be immobilized to a solid support. Proteins are added to the assay which compete with the binding of the antisera to the immobilized antigen. The ability of the above proteins to compete with the binding of the antisera to the immobilized protein is compared to the protein partially encoded by SEQ ID NO:1 or 3. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the above-listed proteins.

The immunoabsorbed and pooled antisera are then used in a competitive binding immunoassay as described above to compare a second protein, such as human white homolog, (GenBank # U34919) to the immunogen protein (i.e., MXR1 of SEQ ID NO: 2). In order to make this comparison, the two proteins are each assayed at a wide range of concentrations and the amount of each protein required to inhibit 50% of the binding of the antisera to the immobilized protein is determined. If the amount of protein required is less than twice the amount of the protein encoded by SEQ ID NO: 2, then the second protein is said to specifically bind to an antibody generated to the MXR1 immunogen.

In addition to using nucleic acid probes for identifying novel forms of the protein claimed herein, it is possible to use antibodies to probe expression libraries. This is a well known technology. (See Young and Davis, 1982 Efficient isolation of genes using antibody probes *Proc. Natl. Acad. Sci., U.S.A.* 80:1194–1198.) In general, a cDNA expression library maybe prepared from commercially available kits or using readily available components. Phage vectors are preferred, but a variety of other vectors are available for the expression of protein. Such vectors include but are not limited to yeast, animal cells and *Xenopus* oocytes. One selects mRNA from a source that is enriched with the target protein and creates cDNA which is then ligated into a vector and transformed into the library host cells for immunoscreening. Screening involves binding and visualization of antibodies bound to specific proteins on cells or immobilized on a solid support such as nitrocellulose or nylon membranes. Positive clones are selected for purification to homogeneity and the isolated cDNA then prepared for expression in the desired host cells. A good general review of this technology can be found in *Methods of Cell Biology* Vol 37 entitled Antibodies in Cell Biology, Ed. DJ Asai pp 369–382, 1993.

Where the antibodies are generated to a a short peptide, the test proteins are optionally denatured to fully test for selective binding and it may be best to measure the test proteins are against proteins of similar size, e.g., one would test a full length monomer against a prototype full length monomer even though the antisera was generated against a peptide of the prototype monomer. This simplifies the test and avoids having to take into account conformational problems and molecular weight/molar concentrations in the determination of the results from the competitive immunoassays.

Assays for Detecting ATP-Binding Cassette Protein Activity and for Identification of Inhibitors of ATP-Binding Cassette Proteins Cells that overexpress ABC proteins (ABCP) have been shown to be resistant to several chemotherapy drugs. These include mitoxantrone, several anthracyclines, rhodamine, daunomycin, SN-38 (the active metabolite of CPT-11), topotecan, and bisantrene. To identify compounds that can reverse the effect of ABCP overexpression, the concentration of drug that inhibits the proliferation of resistant cells by 50% (IC50) can be measured by an assay in the presence and absence of putative inhibitors. Compounds that cause a significant decrease in the IC50 will represent inhibitors and be characterized further.

The assay involves screening for inhibitors of mitoxantrone resistance in cells that overexpress the MXR1 protein, such as S1-M1-80 cells, MCF-7 AdVp3000 cells, or MCF-7 MX100 cells. (see, e.g., Lee et al., J. Cell. Biochem. 65(4):513–526 (1997)) The cells used can be genetically altered cells that have been altered to overexpress the ATP protein.

The cells can be cultured under standard culture conditions, such as those used in Scala et al., (1997) Mol. Pharmacol. 51(6) 1024–33), for MDR or those conditions used in Lee et al., J. Cell. Biochem. 65(4):513–526 (1997), for MCF-7 AdVp3000.

The cells are then contacted with a toxic chemotherapy drug, such as mitoxantrone or daunomycin, in an amount that permits cell survival due to the resistance conferred by the ATP-binding cassette protein. The amount used is preferably from about 30 µM to about 3 mM. The cells are exposed to the drug for a time that is preferably from about 48 hours to about 96 hours. Cell growth is measured for these cells based on sulforhodamine staining measurement. Alternatively, cell growth can be monitored by vital stains, metabolite measurements or counting cell divisions.

One specific way to measure cell viability is by a calorimetric assay (Skehan et al., Natl. Cancer Inst. 82: 1117–1121 (1990)). Cells can be seeded in 96-well plates at 1000 cells/well, grown for 4 days, and fixed in 50% trichloroacetic acetic acid for example. The cells can then be stained in 0.4% sulphorhodamine B dissolved in 1% acetic acid. After washing, the bound dye can be solubilized with 10 nM unbuffered Tris base, preferably at pH 10.5. The number of viable cells can then be determined by measuring the OD at 570 nm. Alternatively, viability of cells can be measured by counting cells with a cell counter or by incorporation of tritiated thymidine.

The cells are then contacted with a compound that inhibits the biological activity of the ATP-binding cassette protein. Examples of such an inhibitor include, but are not limited to, drugs identified as chemosensitzers which are able to restore sensitivity to cytotoxic agents by inhibiting the transport of PgP substrates. These include, but are not limited to, calcium channel antagonists, antiarrhythmics, antihypertensives, diterpenes, cyclosporines, and many others. The potential inhibitor would be applied to the cell in an amount from about 1 µM to about 1 mM, for a time between about 48 and about 72 hours.

The inhibition of drug resistance can then be detected by measuring the growth inhibition of cells, using a variety of means, such as IC50 measurements, vital staining, metabolite measurements, or confocal microscopy. Confocal microscopy can be used to determine whether a particular drug has been retained or accumulated in the cell.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Cloning of ATP-Binding Cassette Protein MXR1 cDNA libraries constructed with the SuperScript Plasmid System for cDNA Synthesis and Plasmid Cloning (GIBCO-BRL, Rockville Md.) using mRNA from mitoxantrone resistant S1-M1-80 human colon carcinoma cells can be used to isolate the MXR1 nucleic acids of the invention.

The ABC protein (ABCP) gene can be isolated using primers that flank the coding region of the gene. These primers can be used to amplify cDNA reverse transcribed from placenta RNA. Primers corresponding to SEQ ID NO: 5 or 6 can be used to amplify by PCR a 2284 bp product from placenta cDNA. This product can be cloned into the pGEM-T (Promega Madison, Wis.) vector. The sequence of the clone can be confirmed by DNA sequencing of the clone using the original primers as well as 20 nucleotide primers, 300 bp apart, along the coding region of the ABCP gene.

Example 2

Expression of ATP-Binding Cassette Protein MXR1

The coding region of the MXR1 gene can be cloned into appropriate expression vectors to express the gene in cells. This could be for the purpose of purifying the protein to study its properties or raise antibodies, or to study the properties of the protein overexpressed in a mammalian cell line. The full length coding region of MXR1 can be cloned in the N-terminal to C-terminal orientation into the pBacPAK8 transfer vector (Clontech, Palo Alto, Calif.) vector to express the protein in insect cell cultures. Alternatively the MXR1 gene can be cloned into the pNeoEGFP vector (Clontech, Palo Alto, Calif.) to express the protein in mammalian cells. The expression of the protein can be monitored by tagging the amino or carboxy terminus with an appropriate tag (GFP, his) or the untagged protein can be monitored using polyclonal or monoclonal antiserum specific for the MXR1 protein. The nucleotide and amino acid sequences of MXR1 are provided, respectively, in SEQ ID NO:1 and 3 and SEQ ID NO:2 and 4.

Example 3

Assay for Identification of Inhibitors of Mitoxantrone Resistance

The cells that overexpress MXR1 have been shown to be resistant to several chemotherapy drugs. These include mitoxantrone, several anthracyclines, rhodamine, daunomycin, SN-38 (the active metabolite of CPT-11), topotecan, and bisantrene. To identify compounds that can reverse the effect of MXR1 overexpression, the concentration of drug that inhibits the proliferation of resistant cells by 50% (IC50) will be measured in the presence and absence of putative inhibitors. Compounds that cause a significant decrease in the IC50 will represent inhibitors and be characterized further. For example, S1-M1-80 cells can be incubated in media containing 30 micromolar (IC10) of mitoxantrone and the proliferation of the cells measured by sulforhodamine staining after 96 hours with and without the addition of various potential inhibitors, as a screening assay. Next, for compounds that have potential activity, a formal calculation of the IC50 can be made by incubating the cells in a range of concentrations, diluting 3-fold from 3 mM, again, with and without the inhibitor in question. From this data the IC50 can be calculated. In the absence of a reversal agent, the IC50 is 100 micromolar for the S1M1-80 cells. Compounds that lower the IC50 for mitoxantrone can be tested for their ability to also lower the IC50 for other MXR1-transporting drugs such as adriamycin, topotecan, or bisantrene.

As a preliminary screening assay, we can also evaluate the alteration in accumulation of mitoxantrone by confocal microscopy, or of rhodamine by FACS analysis. The latter assay, popularized by investigators working with Pgp antagonists has been used as a screening tool (see, e.g., Scala, et al., Mol. Pharmacol (1997) 51(6):1024–33). Drug resistant cells are obtained from tissue culture dishes, plated into each well of a 96 well plate and then incubated in 1 mM rhodamine 123. Candidate inhibitors are added 15 minutes before addition of the rhodamine. Cells are then incubated for 1 hour, washed and then resuspended for an efflux period in medium alone, or medium containing the candidate inhibitor. After 30 minutes, the level of rhodamine remaining in the cells is tightly correlated with the inhibition of the transporter. A positive control using energy depletion can be incorporated into this study.

Analysis of mitoxantrone accumulation by confocal microscopy is very straightforward and simple assay, which requires no preincubation. The experiment can be performed literally under the microscope, and a 15 minute accumulation of mitoxantrone obtained. The confocal microscope can be set at a specific sensitivity, and thus quantitative information gathered when the accumulation is performed in the presence and absence of the inhibitor.

REFERENCE 1 (bases 1 to 2719)

AUTHORS Allikmets, R., Gerrard, B., Hutchinson, A. and Dean, M.
TITLE Characterization of the human ABC superfamily: isolation and mapping of 21 new genes using the expressed sequence tags database
JOURNAL Human Molecular Genetics 5, 1649–1655 (1996)

REFERENCE 2 (bases 1 to 2719)

AUTHORS Allilamets, R., Schriml, L. M., Hutchinson, A., Romano-Spica, V. and Dean, M.
TITLE A Human Placenta-Specific ATP-Binding Cassette Gene (ABCP) on Chromosome 4q22 that is Involved in Multidrug Resistance
JOURNAL Cancer Research 58 (1998) In press

```
SEQ ID NO: 1
BASE COUNT    799 a    545 c    564 g    811 t
ORIGIN
        1 tttaggaacg caccgtgcac atgcttggtg gtcttgttaa gtggaaactg ctgctttaga
       61 gtttgtttgg aaggtccggg tgactcatcc caacatttac atccttaatt gttaaagcgc
      121 tgcctccgag cgcacgcatc ctgagatcct gagcctttgg ttaagaccga gctctattaa
      181 gctgaaaaga taaaaactct ccagatgtct tccagtaatg tcgaagtttt tatcccagtg
      241 tcacaaggaa acaccaatgg cttccccgcg acagtttcca atgacctgaa ggcatttact
      301 gaaggagctg tgttaagttt tcataacatc tgctatcgag taaaactgaa gagtggcttt
      361 ctaccttgtc gaaaccagt tgagaaagaa atattatcga atatcaatgg gatcatgaaa
      421 cctggtctca acgccatcct gggacccaca ggtggaggca aatcttcgtt attagatgtc
      481 ttagctgcaa ggaaagatcc aagtggatta tctggagatg ttctgataaa tggagcaccg
      541 cgacctgcca atttcaaatg taattcaggt tacgtggtac aagatgatgt tgtgatgggc
      601 actctgacgg tgagagaaaa cttacagttc tcagcagctc ttcggcttgc aacaactatg
      661 acgaatcatg aaaaaaacga acggattaac agggtcattg aagagttagg tctggataaa
      721 gtggcagact ccaaggttgg aactcagttt atccgtggtg tgtctggagg agaaagaaaa
      781 aggactagta taggaatgga gcttatcact gatccttcca tcttgtcctt ggatgagcct
      841 acaactggct tagactcaag cacagcaaat gctgtccttt tgctcctgaa aaggatgtct
      901 aagcagggac gaacaatcat cttctccatt catcagcctc gatattccat cttcaagttg
      961 tttgatagcc tcaccttatt ggcctcagga agacttatgt tccacgggcc tgctcaggag
     1021 gccttgggat actttgaatc agctggttat cactgtgagg cctataataa ccctgcagac
     1081 ttcttcttgg acatcattaa tggagattcc actgctgtgg cattaaacag agaagaagac
     1141 tttaaagcca cagagatcat agagccttcc aagcaggata gccactcat agaaaaatta
     1201 gcggagattt atgtcaactc ctccttctac aaagagacaa aagctgaatt acatcaactt
     1261 tccgggggtg agaagaagaa gaagatcaca gtcttcaagg agatcagcta caccacctcc
     1321 ttctgtcatc aactcagatg ggtttccaag cgttcattca aaaacttgct gggtaatccc
     1381 caggcctcta tagctcagat cattgtcaca gtcgtactgg gactggttat aggtgccatt
     1441 tactttgggc taaaaaatga ttctactgga atccagaaca gagctggggt tctcttcttc
     1501 ctgacgacca accagtgttt cagcagtgtt tcagccgtgg aactctttgt ggtagagaag
     1561 aagctcttca tacatgaata catcagcgga tactacagag tgtcatctta tttccttgga
     1621 aaactgttat ctgatttatt acccatgagg atgttaccaa gtattatatt tacctgtata
     1681 gtgtacttca tgttaggatt gaagccaaag gcagatgcct tcttcgttat gatgtttacc
     1741 cttatgatgg tggcttattc agccagttcc atggcactgg ccatagcagc aggtcagagt
     1801 gtggtttctg tagcaacact tctcatgacc atctgttttg tgtttatgat gattttttca
     1861 ggtctgttgg tcaatctcac aaccattgca tcttggctgt catggcttca gtacttcagc
     1921 attccacgat atggatttac ggctttgcag cataatgaat ttttgggaca aaacttctgc
```

```
1981 ccaggactca atgcaacagg aaacaatcct tgtaactatg caacatgtac tggcgaagaa 2041 tatttggtaa agcagggcat cgatctctca ccctggggct tgtggaagaa tcacgtggcc 2101 ttggcttgta tgattgttat tttcctcaca attgcctacc tgaaattgtt atttcttaaa 2161 aaatattctt aaatttcccc ttaattcagt atgatttatc ctcacataaa aaagaagcac 2221 tttgattgaa gtattcaatc aagttttttt gttgttttct gttcccttgc catcacactg 2281 ttgcacagca gcaattgttt taaagagata cattttaga aatcacaaca aactgaatta 2341 aacatgaaag aacccaagac atcatgtatc gcatattagt taatctcctc agacagtaac 2401 catggggaag aaatctggtc taatttatta atctaaaaaa ggagaattga attctggaaa 2461 ctcctgacaa gttattactg tctctggcat ttgtttcctc atctttaaaa tgaataggta 2521 ggttagtagc ccttcagtct taatacttta tgatgctatg gtttgccatt atttaatata 2581 tgacaaatgt attaatgcta tactggaaat gtaaaattga aaatatgttg gaaaaaagat 2641 tctgtcttat agggtaaaaa aagccaccgg tgatagaaaa aaaatctttt tgataagcac 2701 attaaagtta atagaactt
```

SEQ ID NO: 2
/translation="MSSSNVEVFIPVSQGNTNGFPATVSNDLKAFTEGAVLSFHNICY

RVKLKSGFLPCRKPVEKLEILSNINGIMKPGLNAILGPTGGGKSSLLDVLAARKDPS

GLSGDVLINGAPRPANFKCNSGYVVQDDVVMGTLTVRENLQFSAALRLATTMT

NHEKNERINRVIEELGLDKVADSKVGTQFIRGVSGGERKRTSIGMELITDPSILSLD

EPTTGLDSSTANAVLLLLKRMSKQGRTIIFSIHQPRYSIFKLFDSLTLLASGRLMFH

GPAQEALGYFESAGYHCEAYNNPADFFLDIINGDSTAVALNREEDFKATEIIEPSK

QDKPLIEKLAEIYVNSSFYKETKAELHQLSGGEKKKKITVFKEISYTTSFCHQLRW

VSKRSFKNLLGNPQASIAQIIVTVVLGLVIGAIYFGLKNDSTGIQNRAGVLFFLTTN

QCFSSVSAVELFVVEKKLFIHEYISGYYRVSSYFLGKLLSDLLPMRMLPSIIFTCIV

YFMLGLKPKADAFFVMMFTLMMVAYSASSMALAIAAGQSVVSVATLLMTICFV

FMMIFSGLLVNLTTIASWLSWLQYFSIPRYGFTALQHNEFLGQNFCPGLNATGNN

PCNYATCTGEEYLVKQGIDLSPWGLWKNHVALACMIVIFLTIAYLKLLFLKKYS"

SEQ ID NO: 3
BASE COUNT 123 a 109 c 108 g 162 t
ORIGIN

```
    1 ttcggcctag gggccgaggc ttatacggcc agttccatgg cactggccat agccacaggc 61 caaagtgtgg tgtctgtagc aacactactc atgacaatcg cttttgtatt tatgatgctc 121 ttttctggcc tcttggtgaa tctcagaacc attgggcctt ggctgtcctg gcttcagtac 181 tttagcattc ctcgatatgg cttcacagct tgcagtata atgaattctt gggacaagag 241 ttttgtccag gattcaatgt aacggacaac agcacttgtg ttaacagcta tgcaatatgt 301 actggtaacg agtacttgat aaatcagggc atcgaactgt caccttgggg actgtggaag 361 aatcatgtgg ccctggcttg tatgattatt atcttcctca caattgccta cctgaaattg 421 ttgtttctta aaaagtattc ttaatttccc ctttaacgga ctattaattg tactccaatt 481 aaatatgggc actttgatta cc
```

SEQ ID NO: 4
/translation="FGLGAEAYTASSMALAIATGQSVVSVATLLMTIAFVFMMLFSGL

LVNLRTIGPWLSWLQYFSIPRYGETALQYNEFLGQEFCPGFNVTDNSTCVNSYAIC

TGNEYLINQGIELSPWGLWKNHVALACMIIFLTIAYLKLLFLKKYS"

-continued

Primer sequences
SEQ ID NO: 5 ABCPF1 (5' ACGCACCGTGCACATGCTTG)

SEQ ID NO: 6 ABCPR1 (5' ACAGTGTGATGGCAAGGGAACAG)

What is claimed is:

1. An isolated ATP-binding cassette protein having the following properties:
   i. conferring mitoxantrone resistance to S1-M1-80 human colon carcinoma cells when expressed in the cells;
   ii. being encoded by a nucleic acid capable of under stringent hybridization conditions specifically hybridizing to a polynucleotide sequence, which encodes the amino acid sequence of SEQ ID NO:2, wherein the stringent hybridization conditions comprise a sodium ion concentration of from about 0.01 to about 1.0 M, a pH of from about 7.0 to about 8.3, and a temperature of about 60° C.; and
   iii. having a molecular weight between about 70 kDa and about 75 kDa.

2. The ATP-binding cassette protein of claim 1 wherein the protein has at least 95% identity to the amino acid sequence depicted in SEQ ID NO:2.

3. The ATP-binding cassette protein of claim 1, wherein the protein comprises the amino acid sequence of SEQ ID NO:2.

4. The ATP-binding cassette protein of claim 1, wherein the nucleic acid comprises the nucleotide sequence of SEQ ID NO:1.

* * * * *

SEQUENCE LISTING

<160> NUMBER OF SEQ ID NOS: 6

<210> SEQ ID NO 1
<211> LENGTH: 2719
<212> TYPE: DNA
<213> ORGANISM: Homo sapiens
<220> FEATURE:
<221> NAME/KEY: CDS
<222> LOCATION: (205)..(2172)
<223> OTHER INFORMATION: MXR1

<400> SEQUENCE: 1

```
tttaggaacg caccgtgcac atgcttggtg gtcttgttaa gtggaaactg ctgctttaga      60
gtttgtttgg aaggtccggg tgactcatcc caacatttac atccttaatt gttaaagcgc     120
tgcctccgag cgcacgcatc ctgagatcct gagcctttgg ttaagaccga gctctattaa     180
gctgaaaaga taaaaactct ccag atg tct tcc agt aat gtc gaa gtt ttt        231
               Met Ser Ser Ser Asn Val Glu Val Phe
                 1               5 atc cca gtg tca caa gga aac acc aat ggc ttc ccc gcg aca gtt tcc       279
Ile Pro Val Ser Gln Gly Asn Thr Asn Gly Phe Pro Ala Thr Val Ser
 10              15                  20                  25 aat gac ctg aag gca ttt act gaa gga gct gtg tta agt ttt cat aac       327
Asn Asp Leu Lys Ala Phe Thr Glu Gly Ala Val Leu Ser Phe His Asn
             30                  35                  40 atc tgc tat cga gta aaa ctg aag agt ggc ttt cta cct tgt cga aaa       375
Ile Cys Tyr Arg Val Lys Leu Lys Ser Gly Phe Leu Pro Cys Arg Lys
         45                  50                  55 cca gtt gag aaa gaa ata tta tcg aat atc aat ggg atc atg aaa cct       423
Pro Val Glu Lys Glu Ile Leu Ser Asn Ile Asn Gly Ile Met Lys Pro
     60                  65                  70 ggt ctc aac gcc atc ctg gga ccc aca ggt gga ggc aaa tct tcg tta       471
Gly Leu Asn Ala Ile Leu Gly Pro Thr Gly Gly Gly Lys Ser Ser Leu
 75                  80                  85 tta gat gtc tta gct gca agg aaa gat cca agt gga tta tct gga gat       519
Leu Asp Val Leu Ala Ala Arg Lys Asp Pro Ser Gly Leu Ser Gly Asp
 90                  95                 100                 105 gtt ctg ata aat gga gca ccg cga cct gcc aat ttc aaa tgt aat tca       567
Val Leu Ile Asn Gly Ala Pro Arg Pro Ala Asn Phe Lys Cys Asn Ser
                110                 115                 120 ggt tac gtg gta caa gat gat gtt gtg atg ggc act ctg acg gtg aga       615
Gly Tyr Val Val Gln Asp Asp Val Val Met Gly Thr Leu Thr Val Arg
            125                 130                 135 gaa aac tta cag ttc tca gca gct ctt cgg ctt gca aca act atg acg       663
Glu Asn Leu Gln Phe Ser Ala Ala Leu Arg Leu Ala Thr Thr Met Thr
        140                 145                 150 aat cat gaa aaa aac gaa cgg att aac agg gtc att gaa gag tta ggt       711
Asn His Glu Lys Asn Glu Arg Ile Asn Arg Val Ile Glu Glu Leu Gly
    155                 160                 165 ctg gat aaa gtg gca gac tcc aag gtt gga act cag ttt atc cgt ggt       759
Leu Asp Lys Val Ala Asp Ser Lys Val Gly Thr Gln Phe Ile Arg Gly
170                 175                 180                 185 gtg tct gga gga gaa aga aaa agg act agt ata gga atg gag ctt atc       807
```

-continued

| | | |
|---|---|---|
| Val Ser Gly Gly Glu Lys Arg Thr Ser Ile Gly Met Glu Leu Ile<br>              190                 195                 200 | | |
| act gat cct tcc atc ttg tcc ttg gat gag cct aca act ggc tta gac<br>Thr Asp Pro Ser Ile Leu Ser Leu Asp Glu Pro Thr Thr Gly Leu Asp<br>        205                 210                 215 | 855 | |
| tca agc aca gca aat gct gtc ctt ttg ctc ctg aaa agg atg tct aag<br>Ser Ser Thr Ala Asn Ala Val Leu Leu Leu Leu Lys Arg Met Ser Lys<br>    220                 225                 230 | 903 | |
| cag gga cga aca atc atc ttc tcc att cat cag cct cga tat tcc atc<br>Gln Gly Arg Thr Ile Ile Phe Ser Ile His Gln Pro Arg Tyr Ser Ile<br>235                 240                 245 | 951 | |
| ttc aag ttg ttt gat agc ctc acc tta ttg gcc tca gga aga ctt atg<br>Phe Lys Leu Phe Asp Ser Leu Thr Leu Leu Ala Ser Gly Arg Leu Met<br>250                 255                 260                 265 | 999 | |
| ttc cac ggg cct gct cag gag gcc ttg gga tac ttt gaa tca gct ggt<br>Phe His Gly Pro Ala Gln Glu Ala Leu Gly Tyr Phe Glu Ser Ala Gly<br>            270                 275                 280 | 1047 | |
| tat cac tgt gag gcc tat aat aac cct gca gac ttc ttg gac atc<br>Tyr His Cys Glu Ala Tyr Asn Asn Pro Ala Asp Phe Phe Leu Asp Ile<br>        285                 290                 295 | 1095 | |
| att aat gga gat tcc act gct gtg gca tta aac aga gaa gaa gac ttt<br>Ile Asn Gly Asp Ser Thr Ala Val Ala Leu Asn Arg Glu Glu Asp Phe<br>    300                 305                 310 | 1143 | |
| aaa gcc aca gag atc ata gag cct tcc aag cag gat aag cca ctc ata<br>Lys Ala Thr Glu Ile Ile Glu Pro Ser Lys Gln Asp Lys Pro Leu Ile<br>315                 320                 325 | 1191 | |
| gaa aaa tta gcg gag att tat gtc aac tcc tcc ttc tac aaa gag aca<br>Glu Lys Leu Ala Glu Ile Tyr Val Asn Ser Ser Phe Tyr Lys Glu Thr<br>330                 335                 340                 345 | 1239 | |
| aaa gct gaa tta cat caa ctt tcc ggg ggt gag aag aag aag aag atc<br>Lys Ala Glu Leu His Gln Leu Ser Gly Gly Glu Lys Lys Lys Lys Ile<br>            350                 355                 360 | 1287 | |
| aca gtc ttc aag gag atc agc tac acc acc tcc ttc tgt cat caa ctc<br>Thr Val Phe Lys Glu Ile Ser Tyr Thr Thr Ser Phe Cys His Gln Leu<br>        365                 370                 375 | 1335 | |
| aga tgg gtt tcc aag cgt tca ttc aaa aac ttg ctg ggt aat ccc cag<br>Arg Trp Val Ser Lys Arg Ser Phe Lys Asn Leu Leu Gly Asn Pro Gln<br>    380                 385                 390 | 1383 | |
| gcc tct ata gct cag atc att gtc aca gtc gta ctg gga ctg gtt ata<br>Ala Ser Ile Ala Gln Ile Ile Val Thr Val Val Leu Gly Leu Val Ile<br>395                 400                 405 | 1431 | |
| ggt gcc att tac ttt ggg cta aaa aat gat tct act gga atc cag aac<br>Gly Ala Ile Tyr Phe Gly Leu Lys Asn Asp Ser Thr Gly Ile Gln Asn<br>410                 415                 420                 425 | 1479 | |
| aga gct ggg gtt ctc ttc ttc ctg acg acc aac cag tgt ttc agc agt<br>Arg Ala Gly Val Leu Phe Phe Leu Thr Thr Asn Gln Cys Phe Ser Ser<br>            430                 435                 440 | 1527 | |
| gtt tca gcc gtg gaa ctc ttt gtg gta gag aag aag ctc ttc ata cat<br>Val Ser Ala Val Glu Leu Phe Val Val Glu Lys Lys Leu Phe Ile His<br>        445                 450                 455 | 1575 | |
| gaa tac atc agc gga tac tac aga gtg tca tct tat ttc ctt gga aaa<br>Glu Tyr Ile Ser Gly Tyr Tyr Arg Val Ser Ser Tyr Phe Leu Gly Lys<br>    460                 465                 470 | 1623 | |
| ctg tta tct gat tta tta ccc atg agg atg tta cca agt att ata ttt<br>Leu Leu Ser Asp Leu Leu Pro Met Arg Met Leu Pro Ser Ile Ile Phe<br>475                 480                 485 | 1671 | |
| acc tgt ata gtg tac ttc atg tta gga ttg aag cca aag gca gat gcc<br>Thr Cys Ile Val Tyr Phe Met Leu Gly Leu Lys Pro Lys Ala Asp Ala<br>490                 495                 500                 505 | 1719 | |

-continued

| | | |
|---|---|---|
| ttc ttc gtt atg atg ttt acc ctt atg atg gtg gct tat tca gcc agt<br>Phe Phe Val Met Met Phe Thr Leu Met Met Val Ala Tyr Ser Ala Ser<br>510                    515                    520 | | 1767 |
| tcc atg gca ctg gcc ata gca gca ggt cag agt gtg gtt tct gta gca<br>Ser Met Ala Leu Ala Ile Ala Ala Gly Gln Ser Val Val Ser Val Ala<br>525                    530                    535 | | 1815 |
| aca ctt ctc atg acc atc tgt ttt gtg ttt atg atg att ttt tca ggt<br>Thr Leu Leu Met Thr Ile Cys Phe Val Phe Met Met Ile Phe Ser Gly<br>540                    545                    550 | | 1863 |
| ctg ttg gtc aat ctc aca acc att gca tct tgg ctg tca tgg ctt cag<br>Leu Leu Val Asn Leu Thr Thr Ile Ala Ser Trp Leu Ser Trp Leu Gln<br>555                    560                    565 | | 1911 |
| tac ttc agc att cca cga tat gga ttt acg gct ttg cag cat aat gaa<br>Tyr Phe Ser Ile Pro Arg Tyr Gly Phe Thr Ala Leu Gln His Asn Glu<br>570                    575                    580                    585 | | 1959 |
| ttt ttg gga caa aac ttc tgc cca gga ctc aat gca aca gga aac aat<br>Phe Leu Gly Gln Asn Phe Cys Pro Gly Leu Asn Ala Thr Gly Asn Asn<br>590                    595                    600 | | 2007 |
| cct tgt aac tat gca aca tgt act ggc gaa gaa tat ttg gta aag cag<br>Pro Cys Asn Tyr Ala Thr Cys Thr Gly Glu Glu Tyr Leu Val Lys Gln<br>605                    610                    615 | | 2055 |
| ggc atc gat ctc tca ccc tgg ggc ttg tgg aag aat cac gtg gcc ttg<br>Gly Ile Asp Leu Ser Pro Trp Gly Leu Trp Lys Asn His Val Ala Leu<br>620                    625                    630 | | 2103 |
| gct tgt atg att gtt att ttc ctc aca att gcc tac ctg aaa ttg tta<br>Ala Cys Met Ile Val Ile Phe Leu Thr Ile Ala Tyr Leu Lys Leu Leu<br>635                    640                    645 | | 2151 |
| ttt ctt aaa aaa tat tct taaatttccc cttaattcag tatgatttat<br>Phe Leu Lys Lys Tyr Ser<br>650                    655 | | 2199 |
| cctcacataa aaagaagca cttttgattga agtattcaat caagtttttt tgttgttttc | | 2259 |
| tgttcccttg ccatcacact gttgcacagc agcaattgtt ttaaagagat acatttttag | | 2319 |
| aaatcacaac aaactgaatt aaacatgaaa gaacccaaga catcatgtat cgcatattag | | 2379 |
| ttaatctcct cagacagtaa ccatggggaa gaaatctggt ctaatttatt aatctaaaaa | | 2439 |
| aggagaattg aattctggaa actcctgaca agttattact gtctctggca tttgtttcct | | 2499 |
| catctttaaa atgaataggt aggttagtag cccttcagtc ttaatacttt atgatgctat | | 2559 |
| ggtttgccat tatttaatat atgacaaatg tattaatgct atactggaaa tgtaaaattg | | 2619 |
| aaaatatgtt ggaaaaaaga ttctgtctta tagggtaaaa aaagccaccg gtgatagaaa | | 2679 |
| aaaaatcttt ttgataagca cattaaagtt aatagaactt | | 2719 |

<210> SEQ ID NO 2
<211> LENGTH: 655
<212> TYPE: PRT
<213> ORGANISM: Homo sapiens

<400> SEQUENCE: 2

Met Ser Ser Ser Asn Val Glu Val Phe Ile Pro Val Ser Gln Gly Asn
1               5                   10                  15

Thr Asn Gly Phe Pro Ala Thr Val Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly

-continued

```
             65                  70                  75                  80
Pro Thr Gly Gly Gly Lys Ser Ser Leu Leu Asp Val Leu Ala Ala Arg
                         85                  90                  95
Lys Asp Pro Ser Gly Leu Ser Gly Asp Val Leu Ile Asn Gly Ala Pro
                100                 105                 110
Arg Pro Ala Asn Phe Lys Cys Asn Ser Gly Tyr Val Gln Asp Asp
                115                 120                 125
Val Val Met Gly Thr Leu Thr Val Arg Glu Asn Leu Gln Phe Ser Ala
        130                 135                 140
Ala Leu Arg Leu Ala Thr Thr Met Thr Asn His Glu Lys Asn Glu Arg
145                 150                 155                 160
Ile Asn Arg Val Ile Glu Glu Leu Gly Leu Asp Lys Val Ala Asp Ser
                165                 170                 175
Lys Val Gly Thr Gln Phe Ile Arg Gly Val Ser Gly Gly Glu Arg Lys
                180                 185                 190
Arg Thr Ser Ile Gly Met Glu Leu Ile Thr Asp Pro Ser Ile Leu Ser
                195                 200                 205
Leu Asp Glu Pro Thr Thr Gly Leu Asp Ser Ser Thr Ala Asn Ala Val
210                 215                 220
Leu Leu Leu Leu Lys Arg Met Ser Lys Gln Gly Arg Thr Ile Ile Phe
225                 230                 235                 240
Ser Ile His Gln Pro Arg Tyr Ser Ile Phe Lys Leu Phe Asp Ser Leu
                245                 250                 255
Thr Leu Leu Ala Ser Gly Arg Leu Met Phe His Gly Pro Ala Gln Glu
                260                 265                 270
Ala Leu Gly Tyr Phe Glu Ser Ala Gly Tyr His Cys Glu Ala Tyr Asn
                275                 280                 285
Asn Pro Ala Asp Phe Phe Leu Asp Ile Ile Asn Gly Asp Ser Thr Ala
                290                 295                 300
Val Ala Leu Asn Arg Glu Glu Asp Phe Lys Ala Thr Glu Ile Ile Glu
305                 310                 315                 320
Pro Ser Lys Gln Asp Lys Pro Leu Ile Glu Lys Leu Ala Glu Ile Tyr
                325                 330                 335
Val Asn Ser Ser Phe Tyr Lys Glu Thr Lys Ala Glu Leu His Gln Leu
                340                 345                 350
Ser Gly Gly Glu Lys Lys Lys Ile Thr Val Phe Lys Glu Ile Ser
                355                 360                 365
Tyr Thr Thr Ser Phe Cys His Gln Leu Arg Trp Val Ser Lys Arg Ser
                370                 375                 380
Phe Lys Asn Leu Leu Gly Asn Pro Gln Ala Ser Ile Ala Gln Ile Ile
385                 390                 395                 400
Val Thr Val Val Leu Gly Leu Val Ile Gly Ala Ile Tyr Phe Gly Leu
                405                 410                 415
Lys Asn Asp Ser Thr Gly Ile Gln Asn Arg Ala Gly Val Leu Phe Phe
                420                 425                 430
Leu Thr Thr Asn Gln Cys Phe Ser Ser Val Ser Ala Val Glu Leu Phe
                435                 440                 445
Val Val Glu Lys Lys Leu Phe Ile His Glu Tyr Ile Ser Gly Tyr Tyr
        450                 455                 460
Arg Val Ser Ser Tyr Phe Leu Gly Lys Leu Leu Ser Asp Leu Leu Pro
465                 470                 475                 480
Met Arg Met Leu Pro Ser Ile Ile Phe Thr Cys Ile Val Tyr Phe Met
                485                 490                 495
```

-continued

```
Leu Gly Leu Lys Pro Lys Ala Asp Ala Phe Val Met Met Phe Thr
            500                 505                 510
Leu Met Met Val Ala Tyr Ser Ala Ser Ser Met Ala Leu Ala Ile Ala
            515                 520                 525
Ala Gly Gln Ser Val Val Ser Val Ala Thr Leu Leu Met Thr Ile Cys
            530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
                565                 570                 575
Gly Phe Thr Ala Leu Gln His Asn Glu Phe Leu Gly Gln Asn Phe Cys
            580                 585                 590
Pro Gly Leu Asn Ala Thr Gly Asn Asn Pro Cys Asn Tyr Ala Thr Cys
            595                 600                 605
Thr Gly Glu Glu Tyr Leu Val Lys Gln Gly Ile Asp Leu Ser Pro Trp
            610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
                645                 650                 655
```

<210> SEQ ID NO 3
<211> LENGTH: 502
<212> TYPE: DNA
<213> ORGANISM: Mus sp.
<220> FEATURE:
<221> NAME/KEY: CDS
<222> LOCATION: (1)..(444)
<223> OTHER INFORMATION: MXR1

<400> SEQUENCE: 3

```
ttc ggc cta ggg gcc gag gct tat acg gcc agt tcc atg gca ctg gcc      48
Phe Gly Leu Gly Ala Glu Ala Tyr Thr Ala Ser Ser Met Ala Leu Ala
  1               5                  10                  15 ata gcc aca ggc caa agt gtg gtg tct gta gca aca cta ctc atg aca      96
Ile Ala Thr Gly Gln Ser Val Val Ser Val Ala Thr Leu Leu Met Thr
                 20                  25                  30 atc gct ttt gta ttt atg atg ctc ttt tct ggc ctc ttg gtg aat ctc     144
Ile Ala Phe Val Phe Met Met Leu Phe Ser Gly Leu Leu Val Asn Leu
             35                  40                  45 aga acc att ggg cct tgg ctg tcc tgg ctt cag tac ttt agc att cct     192
Arg Thr Ile Gly Pro Trp Leu Ser Trp Leu Gln Tyr Phe Ser Ile Pro
         50                  55                  60 cga tat ggc ttc aca gct ttg cag tat aat gaa ttc ttg gga caa gag     240
Arg Tyr Gly Phe Thr Ala Leu Gln Tyr Asn Glu Phe Leu Gly Gln Glu
 65                  70                  75                  80 ttt tgt cca gga ttc aat gta acg gac aac agc act tgt gtt aac agc     288
Phe Cys Pro Gly Phe Asn Val Thr Asp Asn Ser Thr Cys Val Asn Ser
                 85                  90                  95 tat gca ata tgt act ggt aac gag tac ttg ata aat cag ggc atc gaa     336
Tyr Ala Ile Cys Thr Gly Asn Glu Tyr Leu Ile Asn Gln Gly Ile Glu
            100                 105                 110 ctg tca cct tgg gga ctg tgg aag aat cat gtg gcc ctg gct tgt atg     384
Leu Ser Pro Trp Gly Leu Trp Lys Asn His Val Ala Leu Ala Cys Met
        115                 120                 125 att att atc ttc ctc aca att gcc tac ctg aaa ttg ttg ttt ctt aaa     432
Ile Ile Ile Phe Leu Thr Ile Ala Tyr Leu Lys Leu Leu Phe Leu Lys
    130                 135                 140
```

```
                                                          -continued aag tat tct taatttcccc tttaacggac tattaattgt actccaatta         481
Lys Tyr Ser
145 aatatgggca ctttgattac c                                         502

<210> SEQ ID NO 4
<211> LENGTH: 147
<212> TYPE: PRT
<213> ORGANISM: Mus sp.

<400> SEQUENCE: 4

Phe Gly Leu Gly Ala Glu Ala Tyr Thr Ala Ser Ser Met Ala Leu Ala
  1               5                  10                  15

Ile Ala Thr Gly Gln Ser Val Val Ser Val Ala Thr Leu Leu Met Thr
             20                  25                  30

Ile Ala Phe Val Phe Met Met Leu Phe Ser Gly Leu Leu Val Asn Leu
         35                  40                  45

Arg Thr Ile Gly Pro Trp Leu Ser Trp Leu Gln Tyr Phe Ser Ile Pro
 50                  55                  60

Arg Tyr Gly Phe Thr Ala Leu Gln Tyr Asn Glu Phe Leu Gly Gln Glu
 65                  70                  75                  80

Phe Cys Pro Gly Phe Asn Val Thr Asp Asn Ser Thr Cys Val Asn Ser
                 85                  90                  95

Tyr Ala Ile Cys Thr Gly Asn Glu Tyr Leu Ile Asn Gln Gly Ile Glu
            100                 105                 110

Leu Ser Pro Trp Gly Leu Trp Lys Asn His Val Ala Leu Ala Cys Met
        115                 120                 125

Ile Ile Ile Phe Leu Thr Ile Ala Tyr Leu Lys Leu Leu Phe Leu Lys
    130                 135                 140

Lys Tyr Ser
145

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer
      ABCPF1

<400> SEQUENCE: 5
acgcaccgtg cacatgcttg                                            20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:PCR primer
      ABCPR1

<400> SEQUENCE: 6
acagtgtgat ggcaagggaa cag                                        23
```